United States Patent [19]

Batha et al.

[11] B 4,001,102

[45] Jan. 4, 1977

[54] PROCESS FOR GENERATING PERIODIC NON-UNIFORM ELECTRIC FIELD, AND FOR REMOVING POLARIZABLE PARTICULATE MATERIAL FROM FLUID, USING FERROELECTRIC APPARATUS

[75] Inventors: Howard D. Batha, Tonawanda, N.Y.; Leslie E. Cross, State College, Pa.

[73] Assignee: The Carborundum Company, Niagara Falls, N.Y.

[22] Filed: June 23, 1975

[21] Appl. No.: 589,179

[44] Published under the second Trial Voluntary Protest Program on March 23, 1976 as document No. B 589,179.

Related U.S. Application Data

[62] Division of Ser. No. 348,835, April 6, 1973.

[52] U.S. Cl. .................. 204/186; 204/180 R; 204/299 R
[51] Int. Cl.² .............. C25B 7/00; B01D 13/02
[58] Field of Search .............. 204/180 R, 299, 186, 204/185, 184, 188; 210/243

[56] References Cited

UNITED STATES PATENTS

| | | |
|---|---|---|
| 2,555,487 | 6/1951 | Haugaard et al. ............ 204/180 R |
| 3,304,251 | 2/1967 | Walker et al. ................ 204/186 X |
| 3,478,494 | 11/1969 | Lustenader et al. ................ 55/127 |
| 3,496,701 | 2/1970 | Owe Berg .............................. 55/6 |
| 3,687,834 | 8/1972 | Candor .............................. 204/186 |

Primary Examiner—T. Tung
Assistant Examiner—A. C. Prescott
Attorney, Agent, or Firm—David E. Dougherty; Raymond W. Green

[57] ABSTRACT

Polarizable particulate material, such as organic and inorganic colloidal particles such as small pieces of metal, oxides and the like, zwitterionic molecules, and even living organisms and viruses can be preferentially removed from a liquid by dielectrophoresis, by passing the liquid containing the polarizable particulate material to be removed over a ferroelectric apparatus which generates a periodic non-uniform electric field near the boundary between alternately polarized portions of the ferroelectric material. The periodic non-uniform electric field is generated by subjecting portions of the ferroelectric material to an alternating potential to alternately polarize the portions, while allowing other portions of the ferroelectric material to remain polarized in the same direction.

2 Claims, 25 Drawing Figures

PROCESS FOR GENERATING PERIODIC NON-UNIFORM ELECTRIC FIELD, AND FOR REMOVING POLARIZABLE PARTICULATE MATERIAL FROM FLUID, USING FERROELECTRIC APPARATUS

This is a division, of copending application Ser. No. 348,835, filed Apr. 6, 1973.

BACKGROUND OF THE INVENTION

It is well known that if an electric field is generated between two oppositely charged electrodes, any charged particles which are located between the two electrodes will be attracted to the corresponding electrode having a charge opposite that of the particle. This phenomenon is known as electrophoresis. If the particles do not have a net charge, and are polarizable, the electric field will induce a polarization in the particle; for example in a metal particle this results in a shift of electrons to the side of the particle facing the positive electrode. Since the particle is still neutral, although polarized, no movement occurs in a uniform field. The magnitude of the resultant polarization is related to the effective dielectric constant of the material and of the support medium. Materials which have high dielectric constants exhibit large polarizations in the presence of an electric field. Materials which have a low dielectric constant, on the other hand, develop much lower polarization in the presence of an electric field.

If the particles are placed between two oppositely charged electrodes which produce a non-uniform field, such as that produced when one electrode is a point or line and the other electrode is a plane, the polarized particles will experience a net force tending to move the particle into the region of higher electric field strength, assuming the dielectric constant of the particle is greater than that of the medium in which it is located. It may be noted that the direction of the force is not dependent upon the sign of the electric field but is always in the direction of the field gradient. This motion of matter caused by polarization effects in a non-uniform electric field is known as "dielectrophoresis". The principle of dielectrophoresis has been utilized in various types of apparatus to remove polarizable particles from fluids, by passing the fluid containing the polarizable particles to be removed between two dissimilar electrodes, between which is generated a non-uniform electric field. The most popular electrode configuration for such particle separation apparatus appears to be the concentric cylinder configuration or some variant of it, such as a single wire in the center of a surrounding cylindrical electrode. Other electrode configurations have been used, however. All of these various prior art apparatuses appear to have in common the feature of passing the fluid containing the polarizable particles to be separated between two electrodes which have a configuration other than parallel planes, so that a non-uniform electric field is formed between the electrodes when a current is applied to them.

SUMMARY OF THE INVENTION

According to the present invention, there is provided a process and apparatus for removing polarizable particulate material from a fluid. The apparatus comprises a ferroelectric material, polarizable in directions perpendicular to the surfaces of the ferroelectric material, as more fully hereinafter described; a plurality of electrodes, applied to opposite sides of the ferroelectric material; a source of alternating potential, connectable to the electrodes; and means for positioning the fluid containing the polarizable particulate material to be removed in the periodic non-uniform electric field which is generated by the apparatus, while the field is being generated. The ferroelectric material, electrodes and source of alternating current are arranged such that the ferroelectric material comprises at least one portion, preferably a plurality of portions, the direction of polarization of which is to be alternated during generation of the periodic non-uniform field. The ferroelectric material also comprises at least one portion, and again preferably a plurality of portions, the direction of polarization of which is to remain the same during the generation of the periodic non-uniform electric field.

More generally, the present invention also provides an apparatus and process for generating a periodic non-uniform electric field external to the field-generating electrodes, whether for use in a particle extraction apparatus or for other purposes.

BRIEF DESCRIPTION OF THE DRAWINGS

In particular, FIGS. 2–3 illustrate the condition in which no field is present inside or outside the element.

FIGS. 4–5 illustrate the condition in which the positive field, less than the coercive field ($E_c$) is applied to the element, so that no polarization switching has yet occurred.

FIGS. 6–7 illustrate the condition in which a positive field, greater than the coercive field $E_c$, is applied to the element, so that the direction of polarization under the electrodes is completely switched.

FIGS. 8–9 illustrate the condition in which an even greater positive field is applied to the element, so that significant switching is induced beyond the edge of the electrodes.

FIGS. 10–11 illustrate the condition in which the applied field is again reduced to 0.

Figure 1:
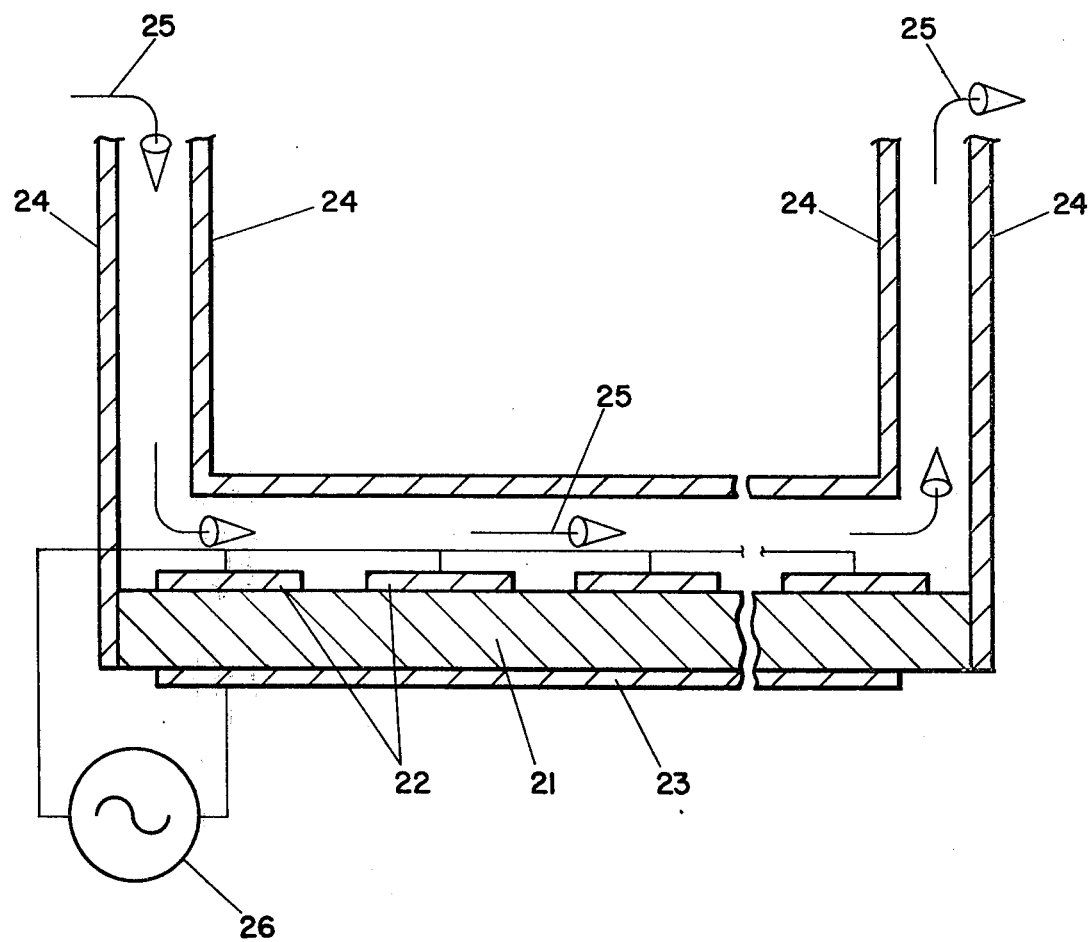
FIG. 1 is a schematic illustration of one type of dielectrophoresis particle extraction apparatus, in accordance with the present invention.

Throughout the drawings the following conventions are used: Arrows with conical heads indicate fluid flow. Solid arrows with ordinary heads indicate directions of polarization. Double-headed arrows indicate alternated directions of polarization. Dotted arrows indicate electric fields.

DETAILED DESCRIPTION

This invention relates to an apparatus and process for generating a periodic non-uniform electric field, and to an apparatus and process for removing polarizable particulate material from a fluid, using the apparatus for generating a periodic non-uniform electric field as an element of the apparatus for removing polarizable particulate material from a fluid.

By a "non-uniform" electric field, it is meant that the lines of force of the electric field are not parallel, and are therefore more concentrated, and the electric field is stronger, in one location than in another. By "periodic" it is meant that the non-uniform electric field is not of constant strength, but becomes stronger and weaker and reverses at various times, passing through a repeated sequence of such values. By "external" it is meant that the place where the periodic non-uniform electric field is generated is located other than between the electrodes which are used to generate the periodic non-uniform electric field.

The central element of the apparatus for generating a periodic non-uniform electric field is a ferroelectric material which is polarizable in directions perpendicular to the surface of the ferroelectric material. "Ferroelectric materials" (or simply "ferroelectrics") are a sub-set of the class of pyroelectric materials, and they have been used for a variety of sophisticated electronic equipment. A ferroelectric material is a pyroelectric material whose polarization can, as a consequence of the crystallographic structure of the ferroelectric, be reversed or reoriented by application of a suitably directed electric field of sufficient magnitude. The electric field needed to switch the polarization is a characteristic of the particular ferroelectric utilized. The electric field necessary to switch the direction of polarization is known as the "coercive field" ($E_c$) of the ferroelectric material and may vary with the direction of the crystal orientation with respect to the field direction when the coercive field is measured. In most ferroelectric crystals and ceramics the coercive field is also a function of both form and frequency of the applied field. In fact, depending on the crystallographic structure of the particular ferroelectric material involved, there may not be a coercive field defined in a particular direction because it may be that no amount of electric field applied in that direction will cause a change in the direction of polarization of the ferroelectric material.

Ferroelectric materials which can be utilized for the present invention include various known ferroelectric materials such as barium titanate, triglycine sulfate ("TGS"), triglycine fluoberylate ("TGFB"), barium niobate, strontium niobate, and sodium potassium tartrate tetrahydrate (Rochele salt).

Solid solutions made from suitable ferroelectric end members such as those listed below, can also be employed.

TGS - TGFB
$BaTiO_3$ - $SrTiO_3$
$PbTiO_3$ - $PbZrO_3$
$BaNb_2O_6$ - $SrNb_2O_6$
$BaNb_2O_6$ - $SrTa_2O_6$

For suitable compositions such as $PbTiO_3$-$PbZrO_3$ the ferroelectric may also be used in polycrystalline ceramic form.

For use in the present invention, ferroelectric material polarizable in directions perpendicular to the surface of the ferroelectric material is needed. Ferroelectric materials can have one or more "ferroelectric axes", or directions in which polarization of the ferroelectric material can exist. Some crystals have only a single ferroelectric axis, in which case the crystal can exhibit spontaneous polarizations in only two directions (each direction along the single axis); other crystals have multiple ferroelectric axes, so that spontaneous polarization can exist in several directions. Either type of ferroelectric material, either having a single axis or multiple ferroelectric axes, is useful for the present invention.

Before describing in detail the circuit of the apparatus for generating a periodic non-uniform electric field in accordance with the present invention, one type of apparatus for removing polarizable particulate material from a fluid which utilizes this circuit will be briefly described with reference to FIG. 1.

Referring now to FIG. 1, it is a sectional schematic view of a dielectrophoresis particle extraction apparatus in accordance with the present invention, i.e., an apparatus for removing polarizable particulate material from a fluid. This apparatus comprises a piece of planar ferroelectric material 21 bearing electrodes 22 and 23, planar ferroelectric material 21 serving as one wall of a conduit through which fluid containing polarizable particulate material to be removed is past. The remaining walls 24 of the conduit complete the basic apparatus, except for the electric circuitry described below. In order to utilize this apparatus, the fluid containing the polarizable particulate material to be removed is positioned in the periodic non-uniform electric field while the periodic non-uniform electric field is being generated, in this case by passing the fluid through the periodic non-uniform electric field which is located in the positions between electrodes 22. The path of the fluid through the conduit defined by planar ferroelectric material 21 and walls 24 is indicated by arrows 25.

Figure 2:
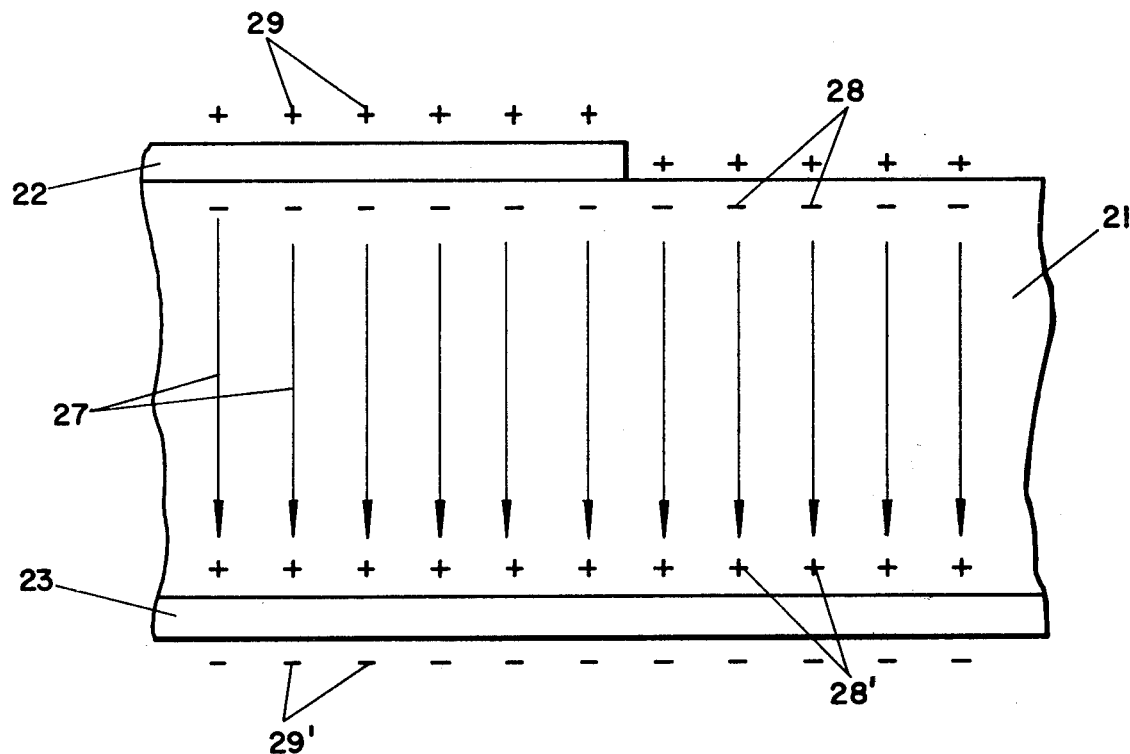
FIGS. 2, 4, 6, 8, and 10 are enlargements of a portion of the electroded ferroelectric material of FIG. 1, illustrating the directions of polarization and field strength under the various conditions of applied field.
Figure 3:
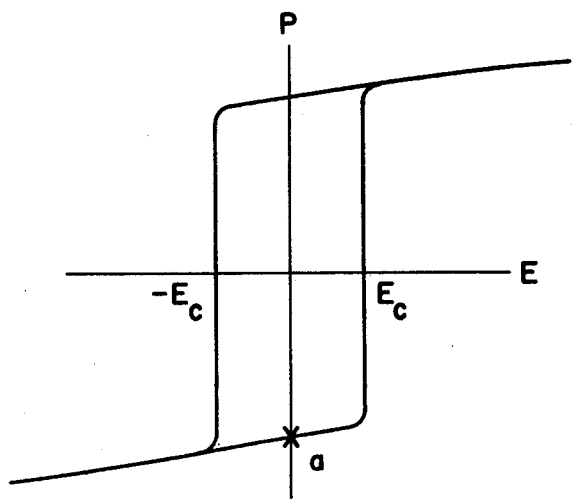
FIGS. 3, 5, 7, 9 and 11 are illustrations of the hysteresis loop which is characteristic of the ferroelectric material of FIG. 1, showing the condition of applied field, E, and polarization, P, for FIGS. 2, 4, 6, 8 and 10, respectively.

To illustrate the influence of the ferroelectric material in generating the very high field gradients necessary for effective dielectrophoretic separation, reference is made to FIGS. 2–11. In these figures, the direction of polarization of the portions of the ferroelectric material are indicated by unbroken arrows, and the direction of field strength is indicated by dotted arrows. It is assumed that before electroding, the ferroelectric crystal (or ceramic) was poled to negative remanence, as shown by the working point a in FIG. 3, then left to equilabrate. After a time which is long compared to the dielectric relaxation time tau of the ferroelectric material 21, the charge situation at the surfaces of ferroelectric material 21 will be as shown in FIG. 2. Unbroken arrows 27 illustrate the spontaneous polarization of ferroelectric material 21 with bound charges 28 and 28' on the surfaces of the ferroelectric material 21. These bound charges will be exactly compensated by "free" surface charges 29 and 29', and no field will exist either inside or outside the piece of ferroelectric material 21.

Figure 4:
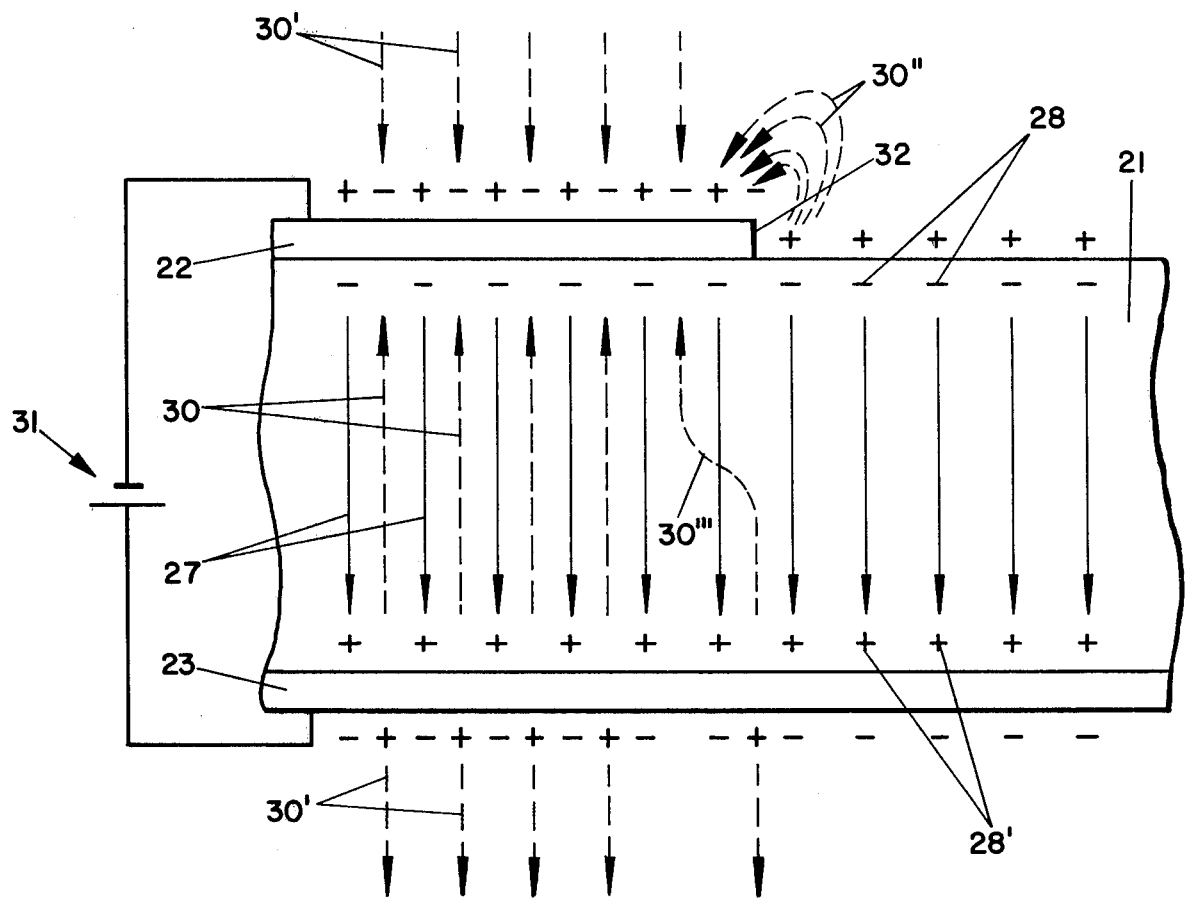
Figure 5:
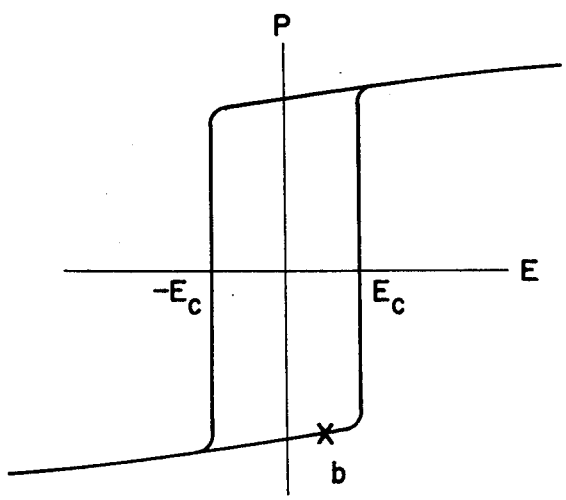

If electrodes 22 and 23 are now connected to a generator which begins to generate a positive field between electrodes 22 and 23, as illustrated in FIG. 4, some positive charge will be applied to electrode 23, negative charge to electrode 22, and a field will be set up in the direction opposing the spontaneous polarization $P_s$ (unbroken polarization arrows 27), as shown by the dotted arrows 30 in FIG. 4. If the voltage applied to electrodes 22 and 23, shown as single cell DC potential source 31, is less than the coercive field $E_c$ of the ferroelectric material 21, the working point will now move out on the hysteresis loop (FIG. 5) to some point b. Electric field as shown by dotted arrows 30 and 30' will now exist both inside and in the space outside the ferroelectric material 21, and a strong field gradient (dotted arrows 30") begins to develop at the edge 32 of electrode 22, on the upper surface of ferroelectric material 21.

Of special importance, however, is the field at the edge 32 but inside the ferroelectric material 21. It can be seen from FIG. 4 that because of the equipotential of the electrode on the lower surface of ferroelectric material 21, the field will tend to spill out (fringe) into the unelectroded portion of the ferroelectric material 21 (see dotted field arrow 30''' of FIG. 4).

Figure 6:
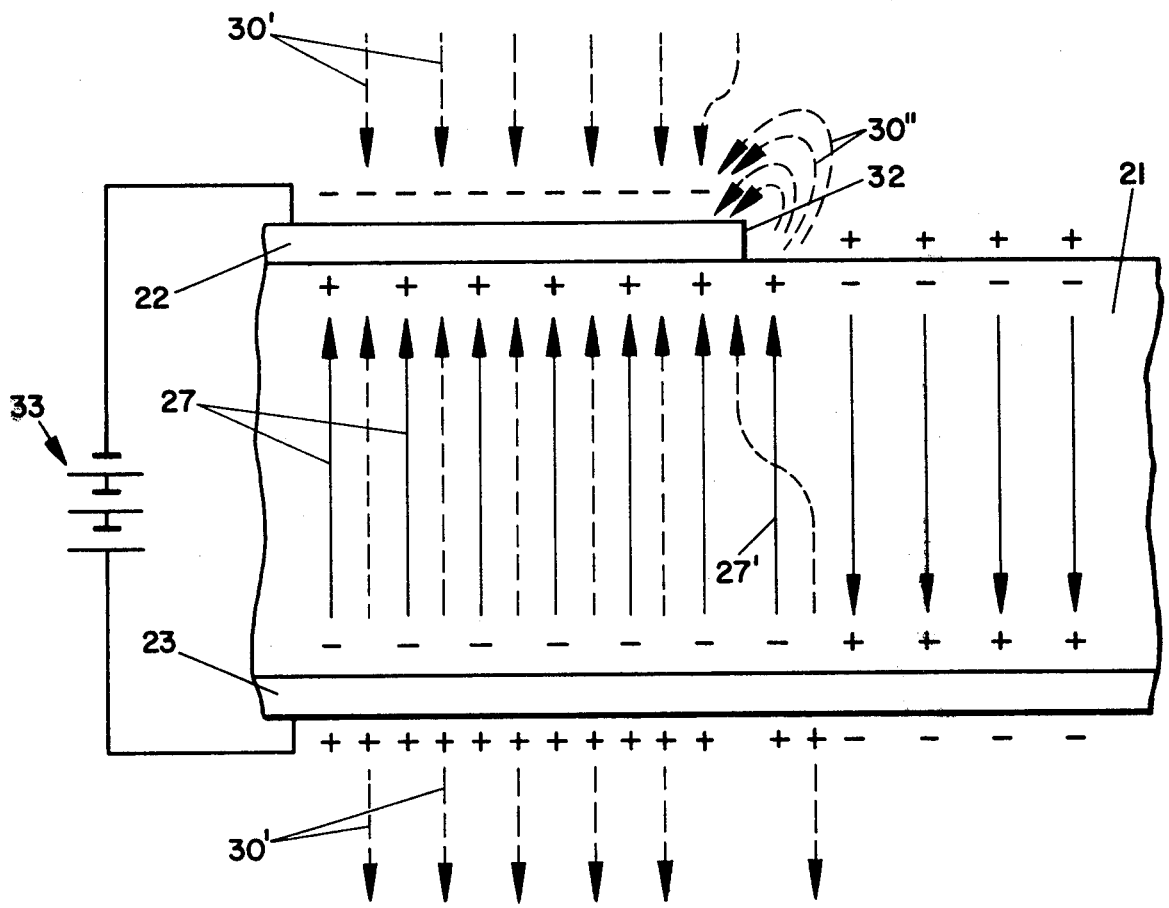
Figure 7:
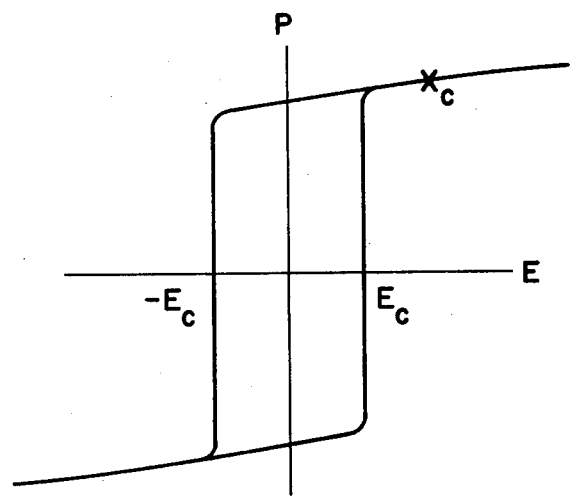

Referring now to FIGS. 6 and 7, if the field is further raised beyond the coercive field $E_c$ necessary for ferroelectric switching, as illustrated by triple cell DC potential source 33 in FIG. 6, for example to point c in FIG. 7, the spontaneous polarization $P_s$ under electrode 22 will now invert (see polarization arrows 27 of FIG. 6). It should be noted that while FIGS. 4, 6 and 8 illustrate the potential applied to electrodes 22 and 23 as DC potential sources, this is merely an indication of the instantaneous potential condition which is in reality supplied by an alternating source of potential.

Massive negative charge must now flow onto electrode 22 to compensate the switching charge associated with the spontaneous polarization which is indicated by polarization arrows 27. However, spillover of the field, together with the continuity of the domain wall, will force some switching beyond edge 32 (see polarization arrow 27' of FIG. 6). Since, however, there is no electrode on this surface above polarization arrow 27', and therefore no contact to the source of potential 33, no free charge will accumulate to compensate the large bound positive charge of the domain switching.

This large positive charge now forms a virtual electrode (accumulation of charge which behaves as an electrode) extremely close to the true negative electrode at edge 32, driving up the surface field to very high values and producing an exceedingly large field gradient at edge 32, as shown by field arrows 30" in FIG. 6.

Figure 8:
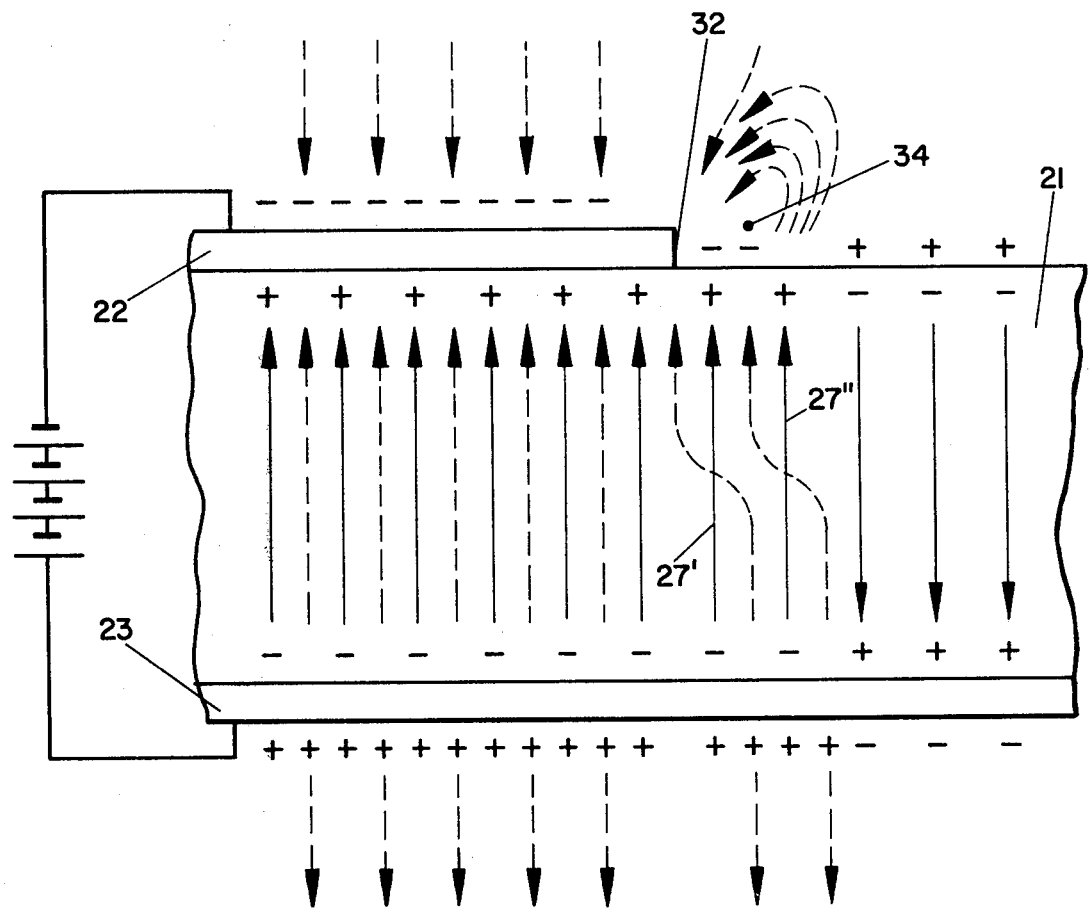
Figure 9:
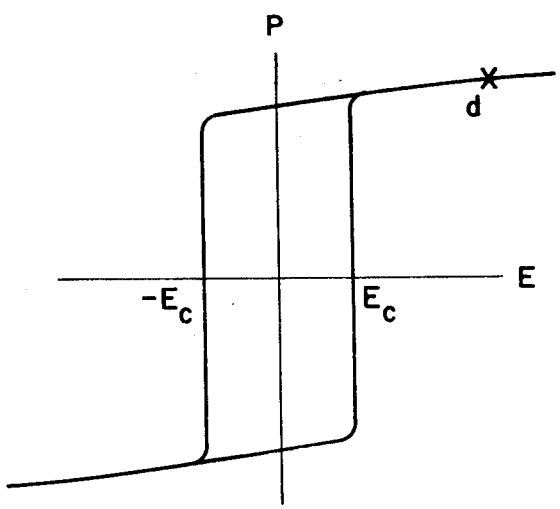

One cardinal advantage of this virtual electrode is shown in FIGS. 8 and 9. If the E field at the surface of the ferroelectric material 21 is now increased further, for example to working point d in FIG. 9, so that further fringe switching is induced (see polarization arrow 27" in FIG. 8), then the E field at the surface at the point indicated by number 34, near the edge 32 of the real electrode, may exceed the breakdown strength of the ambient medium. In this case, carriers will be transported from the negative electrode over the surface. In a normal electroded device, catastrophic short circuit would result. For the circuit under consideration, however, the accumulating negative surface charge simply moves the high field region over, new switching is induced, and a new high field region is generated at point 34.

Figure 10:
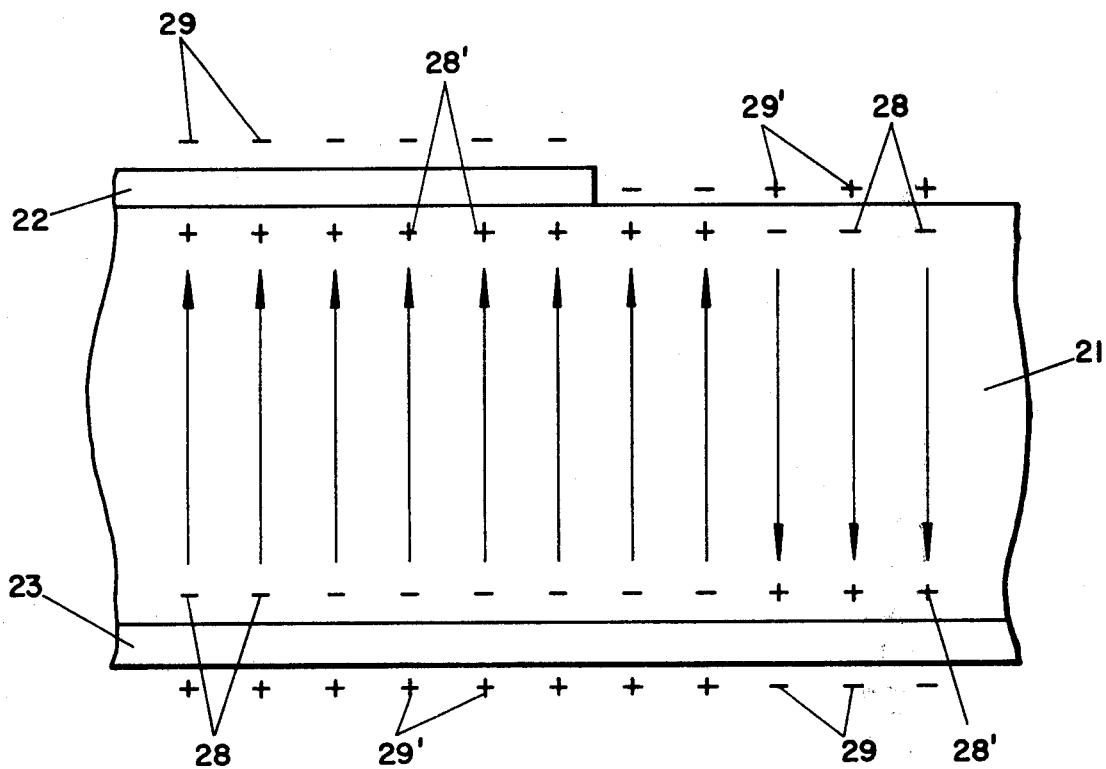
Figure 11:
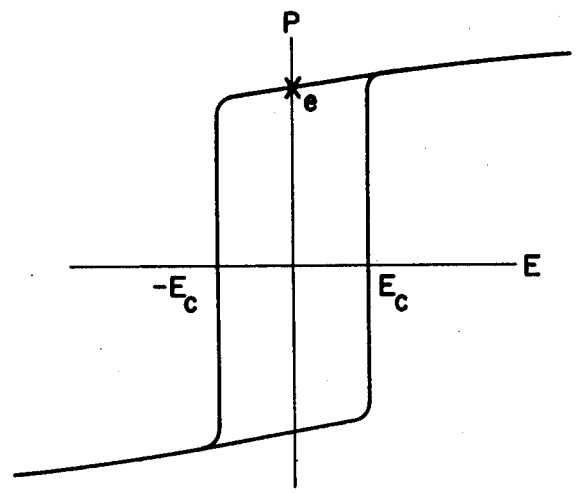

Referring now to FIGS. 10 and 11, when the source of potential has cycled to the point where no field is applied to electrodes 22 and 23, as illustrated by working point e of FIG. 11, the polarization and charge situation will be as shown in FIG. 10. Both the internal and external fields will be absent at this point, and the only charges present will be the bound polarization charges 28 and 28' and the compensating free surface charges 29 and 29'. A new half cycle may now be initiated, with the working point moving around the hysteresis loop at points on the left hand (negative field) side, corresponding to b, c and d in FIGS. 5, 7, and 9, on the right hand side of the hysteresis loops in these figures. The field and polarization effects for this half of the cycle are exactly opposite to those of the half of the cycle illustrated in FIGS. 4–11, with the high intensity field having the same shape but merely the opposite direction.

It may be noted that:

1. The highest field is generated immediately adjacent to the electrode edge 32.
2. The field strength drops away rapidly into the ambient medium, with distances further from electrode edge 32.
3. The sign of the field inverts on each half cycle of the driving field.
4. The field gradient, unlike the field itself, does not change sign, so that the gradient $E^2$ which is responsible for the dielectrophoretic driving force for particle removal goes from zero to its maximum value twice on each cycle of the driving electric field.
5. Breakdown or limited conduction in the ambient medium only serves to transport the region of maximum field (and of the highest field gradient) along the surface of the ferroelectric material 21.

The invention will now be illustrated with two examples.

EXAMPLE 1

Figure 12:
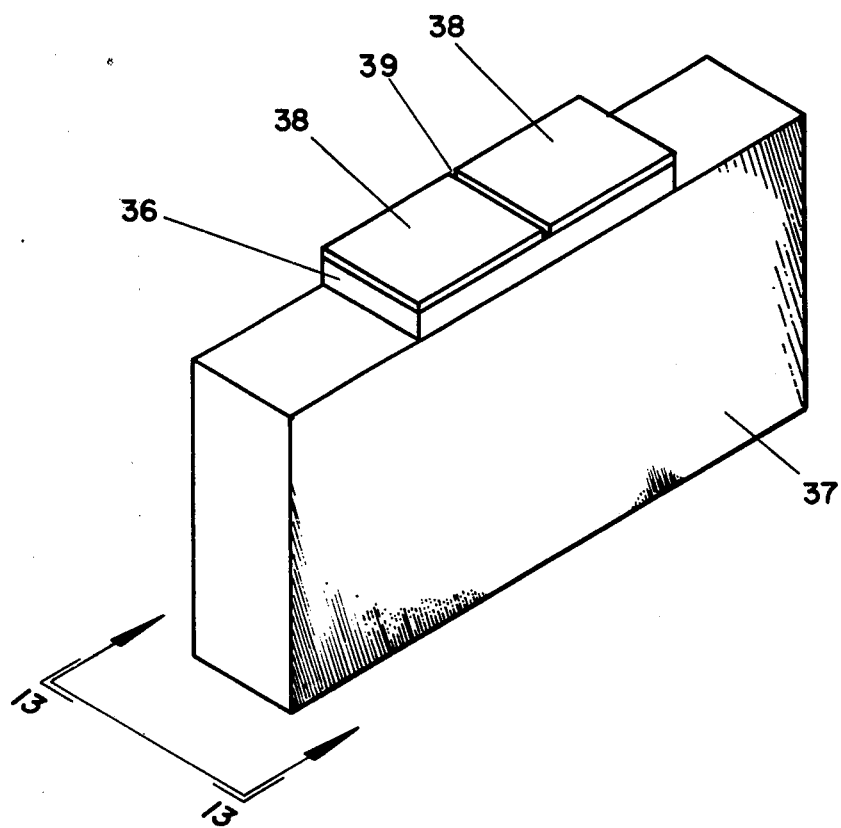
FIG. 12 is a schematic isometric illustration of an electrode configuration for another form of apparatus according to the present invention, for removing polarizable particulate material from a fluid.
Figure 13:
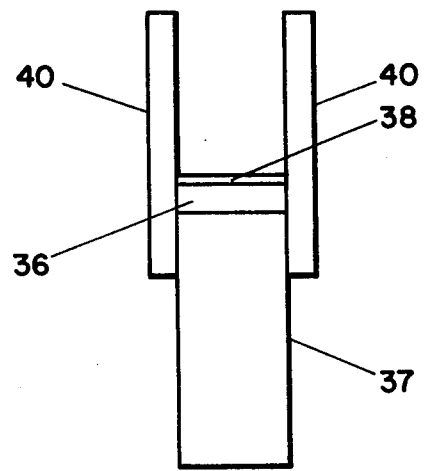
FIG. 13 is a second view of the configuration of FIG. 12, taken along line 13—13 of FIG. 12, and illustrating additional components.

To demonstrate the high field, field gradient and particle separation, referring now to FIG. 12, a piece of ferroelectric material 36 (barium titanate) was mounted upon an alumina substrate 37. The piece of planar ferroelectric material 36 was approximately 50 mm by 1.6 mm and 0.17 mm thick. To the bottom of the piece of planar ferroelectric material 36 as illustrated in FIG. 12, a metallized silver electrode was applied over a 25 mm length center section (not shown in FIG. 12). To the top surface of the piece of planar ferroelectric material 36 was applied a pair of silver electrodes 38, having a thin gap of about 0.25–1.0 mm width. The piece of planar ferroelectric material 36 was then cemented with silver epoxy cement to the alumina substrate 37, suitable electrodes (not shown in FIG. 12) were applied, and the assembly was then enclosed between two glass plates 40 (see FIG. 13). In one end of the cell was mounted a microscope illuminating lamp, and at the other end of the cell a telemicroscope with camera attachment was mounted. Electrical fields were obtained from an audio power amplifier driven by a General Radio unit oscillator, and the amplitude of the voltage applied to electrodes 38, on the one hand, and the electrode on the bottom of the piece of planar ferroelectric material 36 on the other hand, was monitored with a Tektronix oscilloscope and a Hewlett-Packard vacuum tube voltmeter. Glass plates 40 were secured with a room temperature vulcanizing silicone cement.

The completed cell was then filled with a liquid containing acicular polarizable particles suspended in a nonionic insulating liquid. This liquid was Marks Polarized Corporation's Varad Electroopticall Fluid No. V102. This liquid contains needle-like crystalline polarizable particles in a phthalic acid ester base. When randomly distributed, the fluid is opaque, but at well defined field strength and frequency, the crystals can be reoriented parallel to the field and the fluid becomes clear.

A frequency of 4500 cycles alternating potential of a variable voltage was applied to the electrodes on both sides of the planar ferroelectric material 36. As voltage was gradually increased, a small clear area developed about the gap in the top surface electrode 38. This area grew larger with increased voltage and became smaller as the voltage was decreased, and the effect was found to be reproducible. In a second test in similar apparatus, as the voltage was increased, a halo was observed in the vicinity of the gap 39 between the two electrodes 38. Because the planar ferroelectric material had not been fastened securely to the alumina substrate 37 along its entire length, light could be transmitted between the planar ferroelectric material 36 and the alumina substrate 37. At zero volts this area was quite dark. Increasing the voltage to 225 volts (root mean squared) resulted in a clearing of the area. The clear area grew larger at 350 vrms applied to the test cell.

The effect of frequency was not quite as pronounced. Applying a voltage of 225 vrms on the cell, a larger clear area was observed with a frequency of 45000 cycles than was observed with 450 cycles. Each of these observations was reproducible, as well as the halo effect in the gap area.

As a control, a test cell of similar design, but with a glass strip substituted for the planar ferroelectric material 36, was subjected to the same voltage conditions. With 50 vrms applied to the cell, no optical effect was noted. At 100 vrms heating and bubbling of the electro-optical fluid were the only effects observed.

The test was repeated again with a second glass test cell. Again at 30 vrms no optical effect was noted. This was also true at 45000 cycles and at 450 cycles. With 100 vrms applied, slight movement of the particles was observed, indicating a dielectric heating effect. Increasing the voltage to 150 vrms resulted in rapid boiling of the fluid.

It was noted for the ferroelectric cells that after a time of the order of 5 minutes under alternating potential of 225 vrms, the efficiency of the cell as judged by the halo about the electrode gap began to diminish. Stopping the experiment, a thin deposit was observed in the gap region. On removing this deposit with a soft camel's hair brush, the full efficiency was restored. This process was repeated several times, indicating that the strong field gradient was causing the acicular semiconducting particles to be removed from the Marks fluid.

EXAMPLE 2

Figure 14:
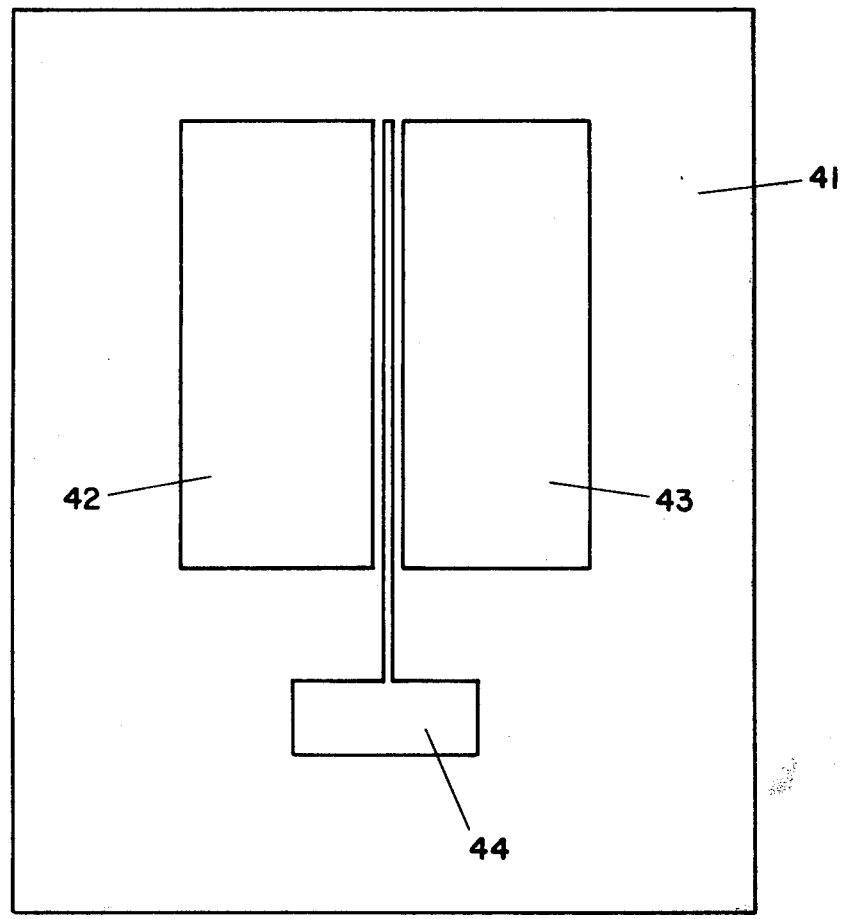
FIG. 14 is a schematic plan view of another form of apparatus according to the present invention, for generating a periodic non-uniform external electric field.

Illustrating the extension of ferroelectric switching into the gap region between electrodes, a piece of planar ferroelectric material, polarizable in directions perpendicular to the plane of the planar ferroelectric material, specifically a lead zirconate - lead titanate produced by Vernatron Piezoelectric, Inc., and identified by them as PZT-5H, was prepared. This piece was 12.7 mm by 15.1 mm and 0.17 mm thick. On this piece of ferroelectric material 41 (see FIG. 14) a series of three electrodes 42–44 were applied to the upper side piece of ferroelectric material 41. Electrode 42 was rectangular, approximately 2.4 mm by 7.1 mm. Electrode 43 was also rectangular, approximately 3.2 mm by 7.1 mm. A space between electrodes 42 and 43 of about 0.25 mm was provided. Midway between electrodes 42 and 43, a narrow strip electrode, the upper portion of electrode 44 as illustrated in FIG. 14, 0.038 mm in thickness, was applied. This electrode was in its entirety of a T-shape as illustrated in FIG. 14.

In operation, electrodes 42 and 43 were connected to an AC generator of 800 volts rms at 60 Hz. Electrode 44 was connected to a 0.22 microfarad integrating capacitor and then directly to the Y-amplifier of a cathode-ray oscilloscope. For this oscilloscope, the x-deflection was provided by a tap from the 60 Hz supply to electrodes 42 and 43.

The appearance of a hysteresis loop on electrode 44 clearly indicated the occurrence of switching of the ferroelectric material 41 within the gap region between electrodes 42 and 43, driven by the fringe field from electrodes 42 and 43. From the quantity of charge switched (about 0.053 microcoulombs, over an area of 0.0028 $cm^2$), it is clear that some 20 microcoulombs/$cm^2$, a major fraction of the spontaneous polarization $P_s$ in this PZT-5H material, was being switched.

Figure 15:
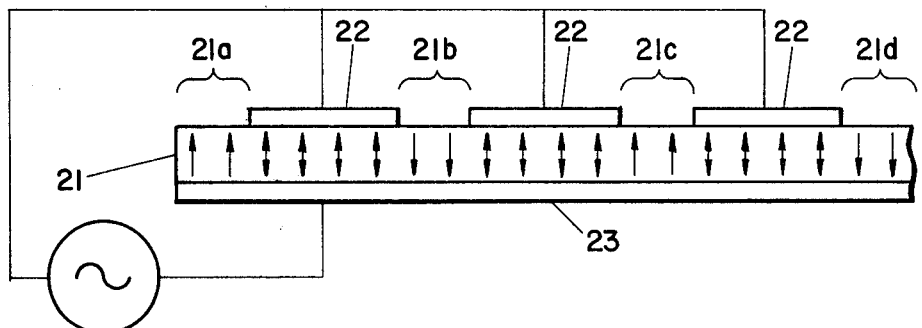
FIG. 15 is a schematic view of another configuration in accordance with the present invention, wherein portions of the ferroelectric material, the direction of polarization of which is to remain the same during generation of the periodic non-uniform electric field, are polarized in alternate directionns perpendicular to the surface of the ferroelectric material.

Other configurations of ferroelectric material can be used, such as successive portions 21a, 21b, 21c, 21d of planar ferroelectric material 21 (see FIG. 15) between successive electrodes 22 being polarized in alternate directions perpendicular to the plane of the planar ferroelectric material. This configuration may have advantages in situations in which a number of parallel plates of ferroelectric material 21 are arranged in close array, so that the overlapping electric fields from adjacent plates can be correlated in their directions. In FIG. 15, as in FIG. 16, the portions of the ferroelectric material whose direction of polarization is alternated are indicated with double-headed arrows, and the directions of polarization of those portions of the ferroelectric material which is not alternated are indicated by singleheaded arrows.

Figure 16:
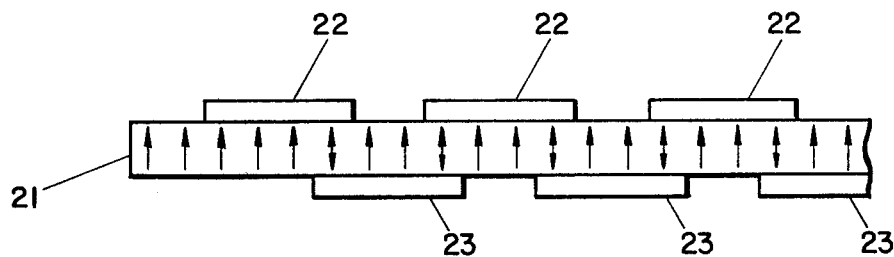
FIG. 16 illustrates another configuration in accordance with the present invention, wherein alternate electrodes are slightly overlapped on opposite sides of the piece of ferroelectrode material.
Figure 17:
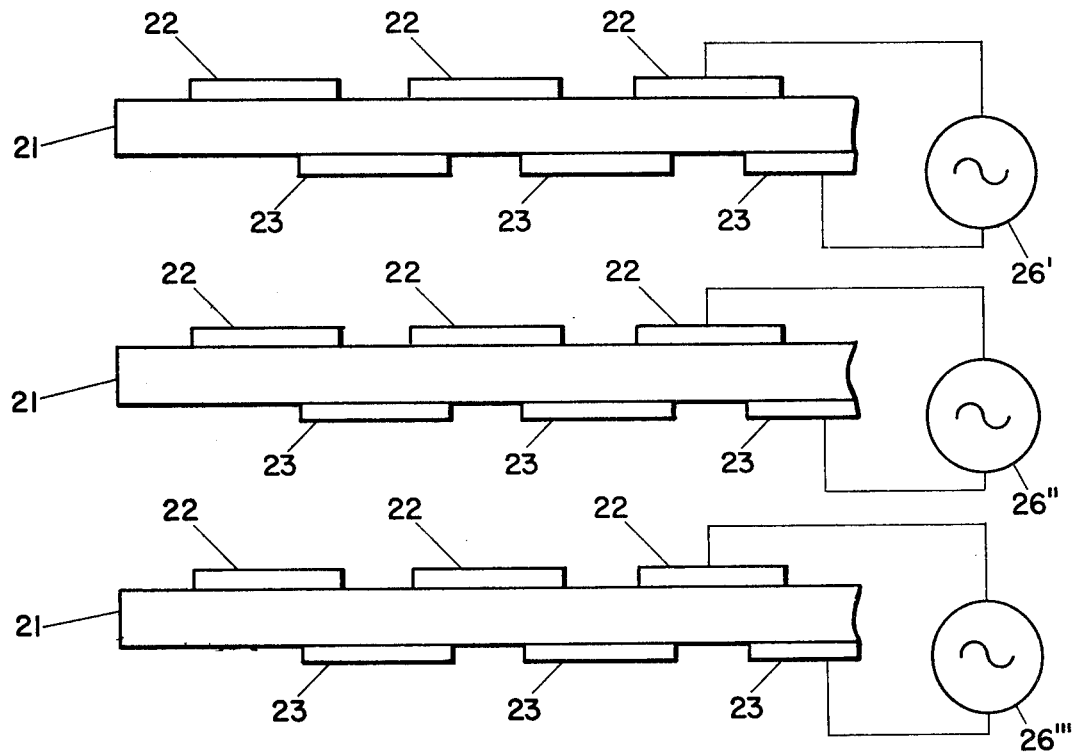
FIGS. 17 and 18 illustrate a configuration of assembling a plurality of pieces of ferroelectrode material in an apparatus for removing particulate polarizable materials from a fluid.

Another configuration is shown in FIG. 16, wherein alternate slightly overlapping electrodes 22, 23 are placed on opposite sides of ferroelectric material 21. An advantage of the configuration shown in FIG. 16 is that the high intensity fields can be generated on both sides of ferroelectric material 21, and in fact a plurality of plates of ferroelectric material 21 as illustrated in FIG. 16 can be arranged in juxtaposition as shown in FIG. 17. Using this configuration, it is possible to connect certain of the electrodes to separate sources of alternating potential, 26', 26'', 26''', so that the various differing portions of the array of ferroelectric materials 21 can be subjected to different phase conditions, and a proper cooperation of the high intensity field locations can be obtained; or so that by utilizing different frequencies, different types of particles which are more responsive to different frequencies can be selectively collected in different locations of the apparatus.

The parallel plate configuration as shown in FIG. 17 can then be placed in a suitable conduit 47 (see FIG. 18), through which the fluid to be purified can be passed as shown by arrows 48.

Figure 19:
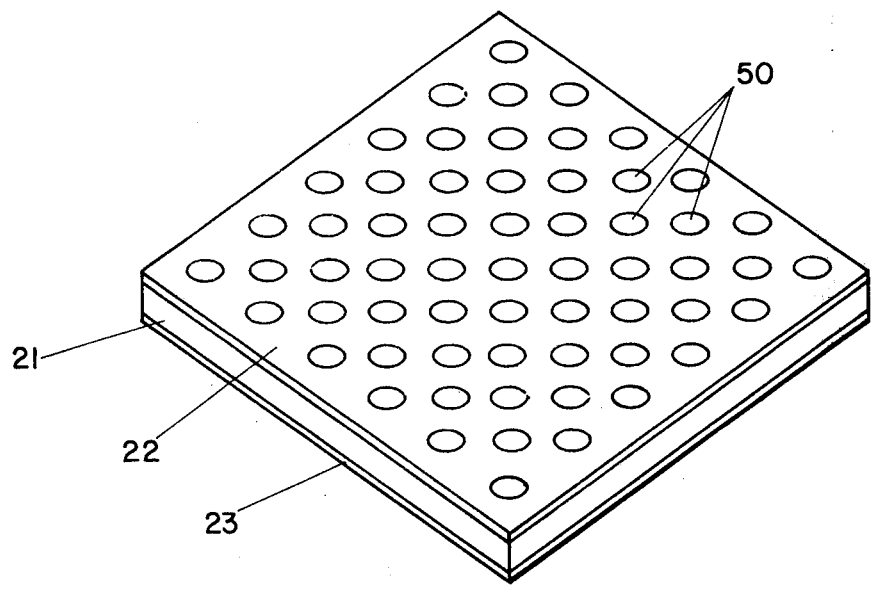
FIG. 19 illustrates an alternative method of forming electroded and non-electroded portions of the surface of the ferroelectric material.

The electrodes need not be in the configuration of parallel stripes, and a polka-dot configuration of nonelectroded portions is illustrated in FIG. 19. The nonelectroded portions 50 can be formed by high spots in the ferroelectric material, so that the entire surface of the ferroelectric material is initially electroded (such as by flashing on gold metallic electrodes by conventional technology), following which the high portions are polished off to remove the unwanted portions of the electrode material. The irregular dimpled shape of the ferroelectric material necessary to produce this configuration can either be formed by pressing the uncured ferroelectric material, prior to firing and polarization, or by sandblasting the cured ferroelectric material after firing. In either case, the high portions of ferroelectric material 21 which is covered by electrode 22 are polished off leaving exposed portions 50 of ferroelectric material 21, which can serve as local cites of particle collection.

Figure 18:
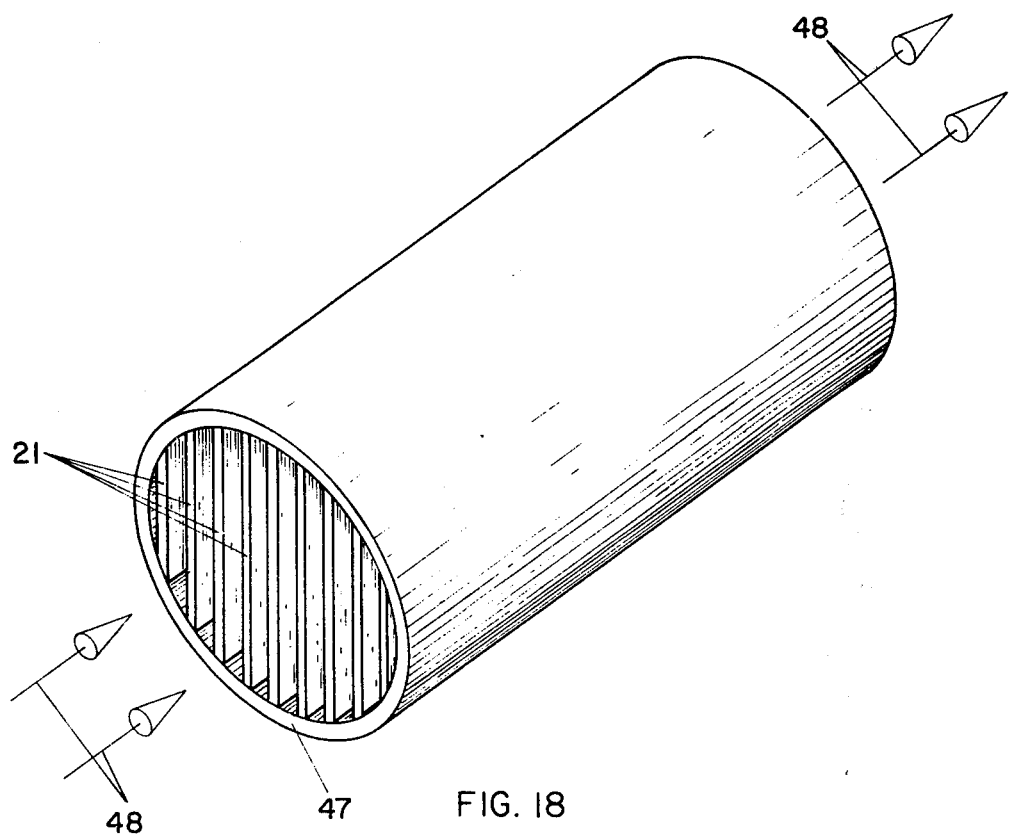
Figure 20:
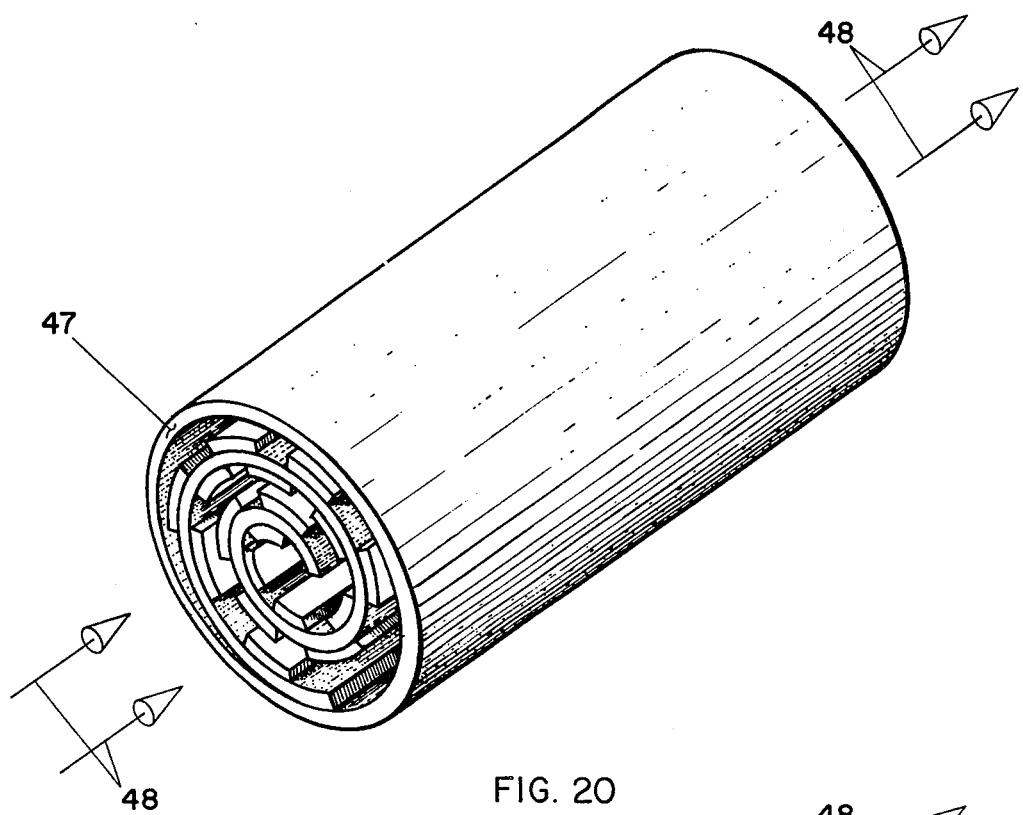
FIGS. 20, 21, and 22 illustrate additional configurations of electrodes and ferroelectric material which can be utilized in the present invention.

Another variant of the apparatus illustrated in FIG. 18 is shown in FIG. 20. Instead of parallel sheets of ferroelectric material, the ferroelectric material with alternate striped electrodes can be arranged in a spiral.

Figure 21:
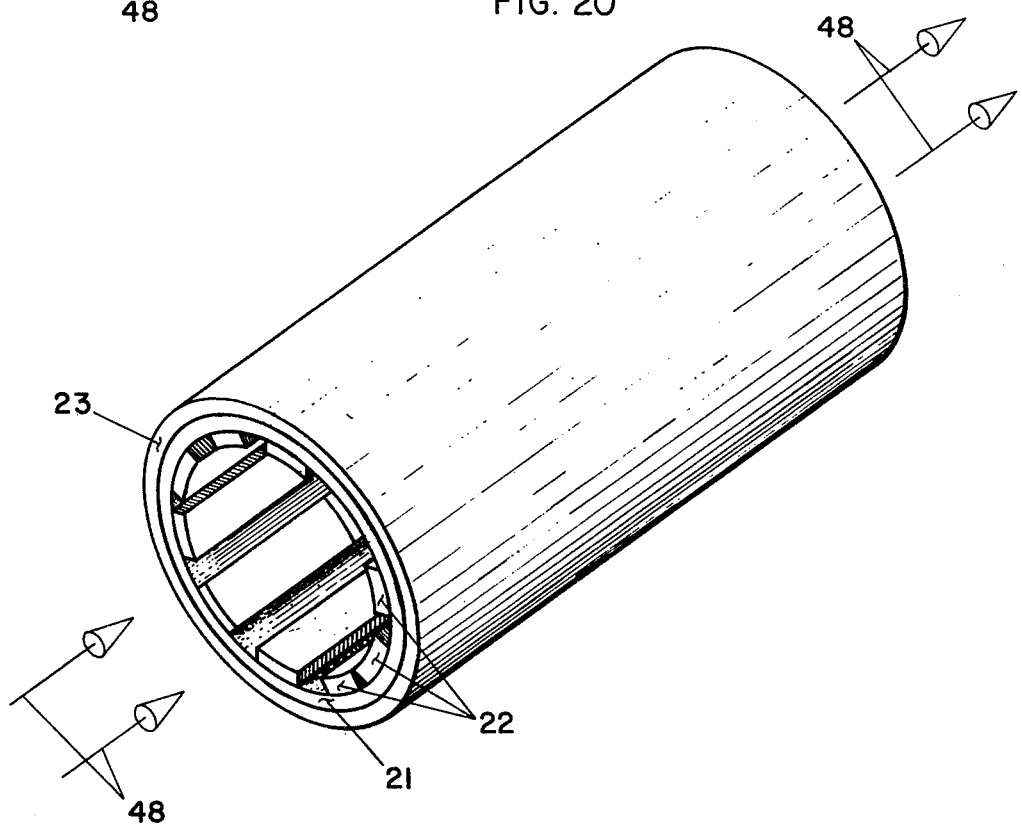

Another approach to using a tube as the conduit is illustrated in FIG. 21, wherein the walls of the conduit are themselves the ferroelectric material, with electrodes being applied inside and outside the conduit. Although the configuration of FIG. 21 is shown with electrodes 22 running parallel to the axis of the ferroelectric conduit 21, other configurations are also possible, such as parallel annular electrodes or spiral electrodes, inside or outside ferroelectric conduit 21.

Figure 22:
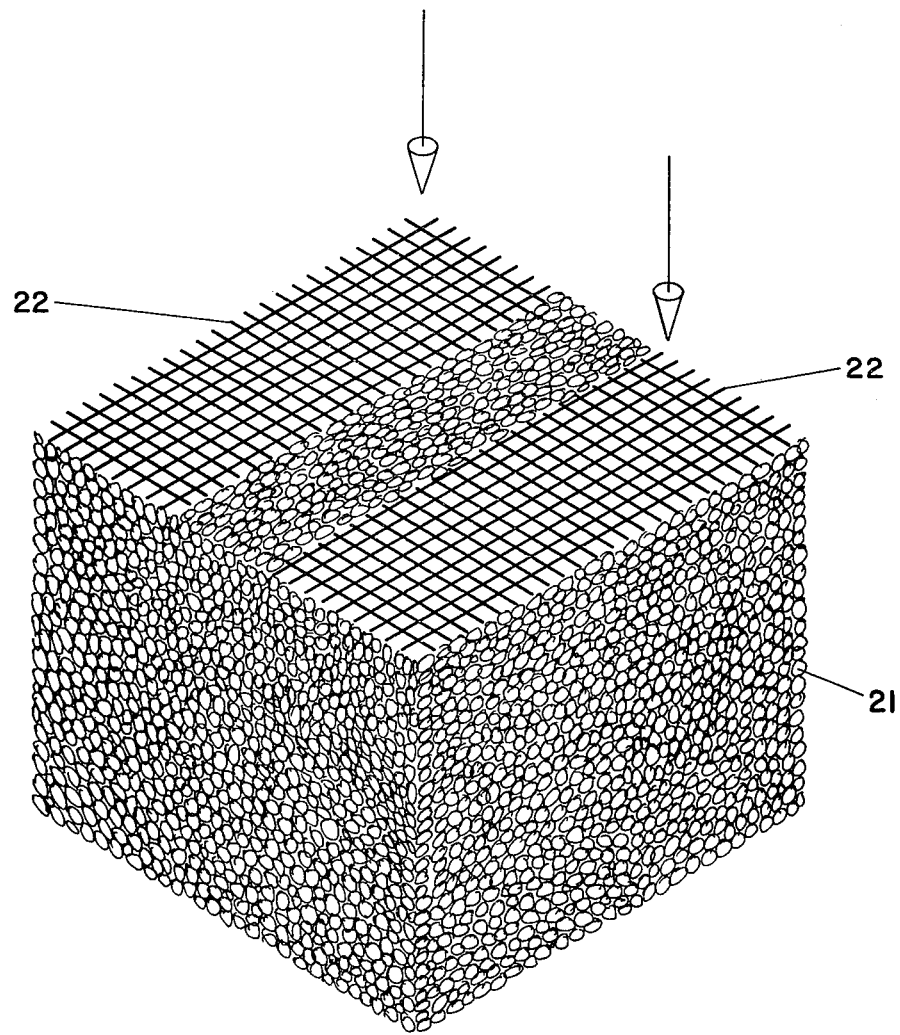

Another approach which can be taken in the construction of ferroelectric bodies for use in the present invention is illustrated in FIG. 22. In this embodiment, small particles of ferroelectric material are sintered lightly together, with random directions of polarization of the individual particles. The porosity of the body as a whole is maintained, so that the liquid to be purified can be passed between the particles, for example from top to bottom as illustrated in FIG. 22. The electrodes can be applied to the surface of the ferroelectric material 21 in a wire mesh configuration, see electrodes 22 of FIG. 22. This allows the passage of fluid directly through the electrodes. Additional electrodes (not shown in FIG. 22), likewise in wire mesh configuration, can be applied to the bottom of the sintered ferroelectric material 21. This configuration has the advantage of combining conventional filter technology with the ferroelectric dielectrophoretic particle removing method according to the present inventon.

Figure 23:
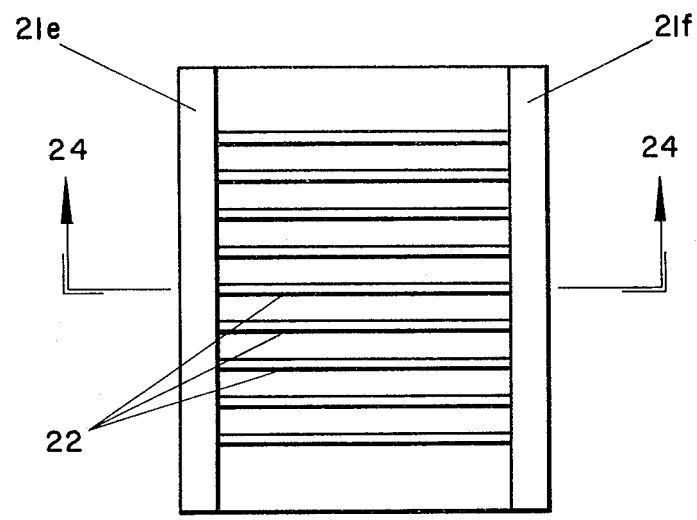
FIGS. 23–25 together illustrate yet another configuration of electrodes and ferroelectric material for use in an apparatus in accordance with the present invention.
Figure 24:
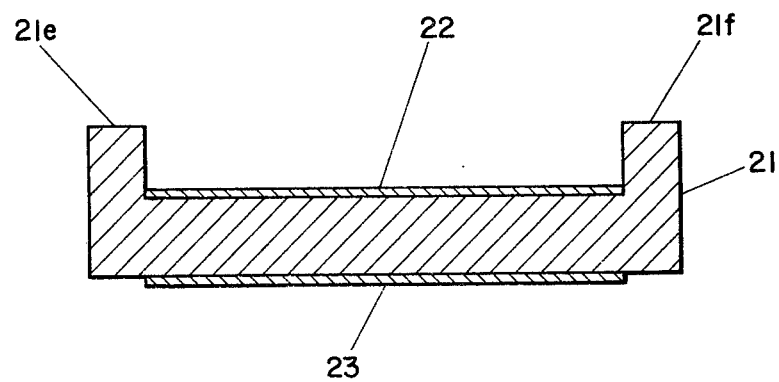
Figure 25:
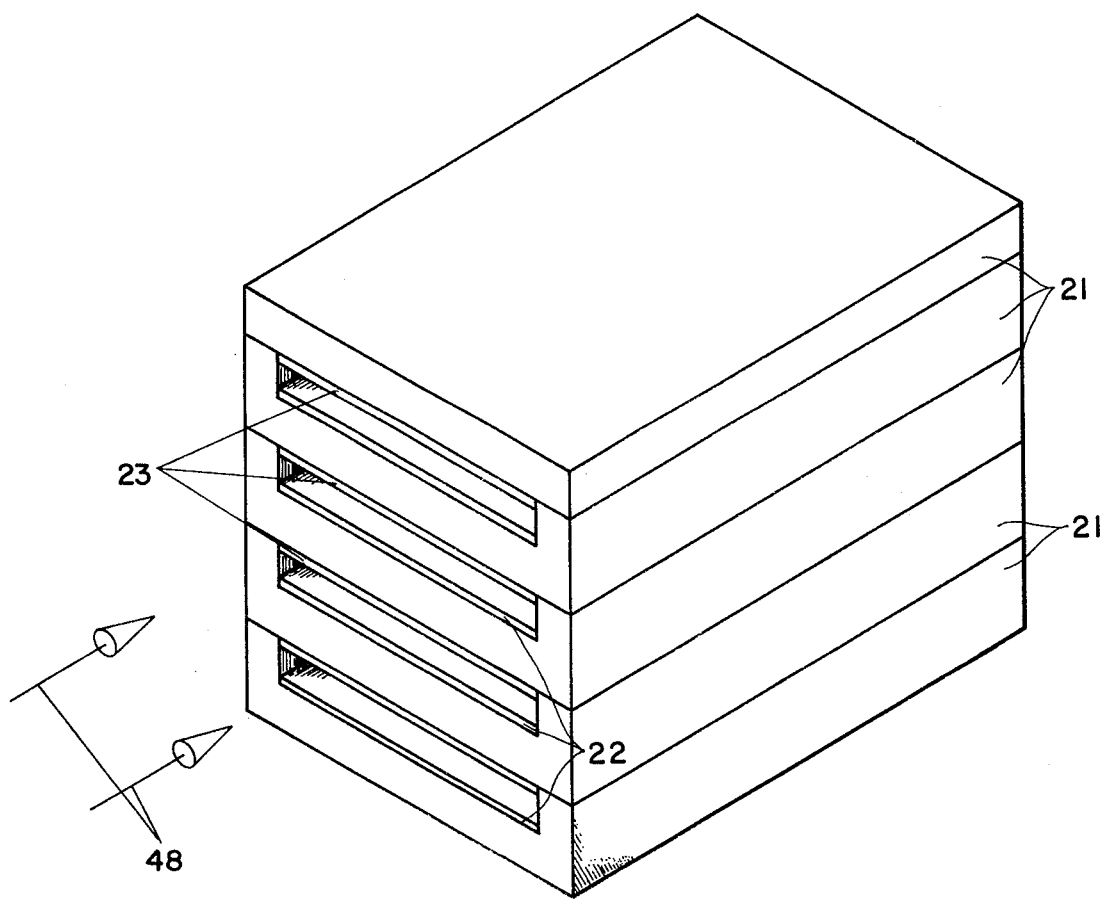

Yet another scheme is illustrated in FIGS. 23–25. A number of individual plates can be fabricated as per FIGS. 23 and 24, each plate consisting of a piece of ferroelectric material 21 which has deposited upon it electrodes 22, 23. For use in this configuration, it is convenient to place a palladium or platinum material on the uncured ferroelectric material 21, together with a material over electrode 22 which can later be leached out by appropriate chemical action. The ferroelectric material 21 and the electrodes 22, 23, together with the material to be leached (not shown in FIG. 24, but present between legs $21e$, $21f$ of ferroelectric material 21), can all be cured together at the same time. A plurality of these plates can then be assembled together in a sandwich configuration as illustrated in FIG. 25, and the material between legs $21e$ and $21f$ can be leached out to form a passage for the fluid to be passed through the apparatus as illustrated by arrows 48 in FIG. 25.

We claim:
1. A process for generating a period non-uniform electric field, external to field-generating electrodes of the apparatus for generating the periodic non-uniform electric field, in an apparatus comprising
 a. a ferroelectric material, polarizable in directions perpendicular to the surface of the ferroelectric material; the ferroelectric material comprising at least one portion, the direction of polarization of which is to be alternated during the generation of the periodic non-uniform electric field, and at least another portion, the direction of polarization of which is to remain the same during the generation of the periodic non-uniform electric field;
 b. a plurality of electrodes, applied to opposite sides of the ferroelectric material, covering both sides of the portions of the ferroelectric material, the direction of polarization of which is to be alternated during the generation of the periodic non-uniform electric field, but leaving uncovered at least one side of the portions of the ferroelectric material so as to produce a non-uniform electric field, the direction of polarization of which is to remain the same during generation of the periodic non-uniform electric field, defining a location external to the field-generating electrodes and adjacent the boundary between the alternately polarized portions of the ferroelectric material, in which the periodic non-uniform electric field is to be generated; and
 c. means for providing alternating potential to the electrodes
  1. for alternating the direction of polarization of the covered portions of the ferroelectric material and leaving polarized in their original direction, the uncovered portions of the ferroelectric material;
  2. for producing periodically alternately polarized portions of the ferrolectric material; and
  3. for generating a periodic non-uniform electric field external to the field-generating electrodes, in the location adjacent the boundary between the alternately polarized portions of the ferroelectric material, said process comprising providing alternating potential to the electrodes on the ferroelectric material in such a way
   a. as to alternate the direction of polarization of the portions of the ferroelectric material, the direction of polarization of which is to be alternated, leaving polarized in their original direction the uncovered portions of the ferroelectric material, the direction of polarization of which is to remain the same;

b. as to produce thereby, periodically, alternately polarized portions of the ferroelectric material; and c. as to generate thereby, a periodic non-uniform electric field, external to the field-generating electrodes, in the location adjacent the boundary between the alternately polarized portions of the ferroelectric material.

2. A process for removing polarizable particulate material from a fluid in a ferroelectric apparatus as described in claim 1, comprising the steps of a. passing the fluid containing the polarizable particulate material to be removed through the periodic non-uniform electric field while the periodic non-uniform electric field is being generated, whereby to concentrate the polarizable particulate material in locations of the most intense periodic non-uniform electric field; and b. periodically discontinuing the generation of the periodic non-uniform electric field, and flushing the apparatus with a cleaning fluid, whereby to remove the concentrated polarizable particulate material from the apparatus.

* * * * *